(12) United States Patent
Wei

(10) Patent No.: US 7,476,127 B1
(45) Date of Patent: Jan. 13, 2009

(54) ADAPTER FOR MINI-COAXIAL CABLE

(75) Inventor: Kai-Chih Wei, Taipei (TW)

(73) Assignee: Ezconn Corporation, Taipei (TW)

( * ) Notice: Subject to any disclaimer, the term of this patent is extended or adjusted under 35 U.S.C. 154(b) by 0 days.

(21) Appl. No.: 12/007,281

(22) Filed: Jan. 9, 2008

(51) Int. Cl.
H01R 9/05 (2006.01)

(52) U.S. Cl. ....................................... 439/583
(58) Field of Classification Search ................ 439/578, 439/583, 584
See application file for complete search history.

(56) References Cited

U.S. PATENT DOCUMENTS 7,153,159 B2 * 12/2006 Burris et al. ................ 439/578

* cited by examiner

Primary Examiner—Tho D Ta
(74) Attorney, Agent, or Firm—Rosenberg, Klein & Lee

(57) ABSTRACT

An adapter for mini-coaxial cable includes a cylindrical member for receiving a length of exposed insulating spacer of a mini-coaxial cable therein, and an electrically conductive insertion member for receiving a bare center conductor of the mini-coaxial cable therein so as to provide sufficient rigid support to the thin center conductor. When the adapter is inserted into a standard coaxial cable connector, the insertion member is radially compressed by the connector to thereby tightly grip the bare center conductor.

7 Claims, 5 Drawing Sheets

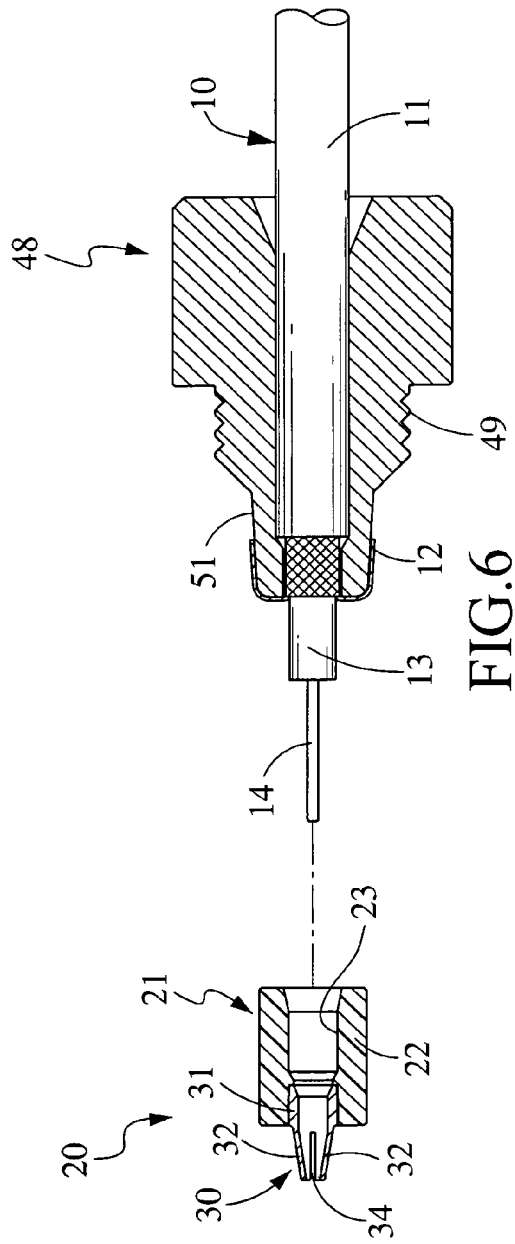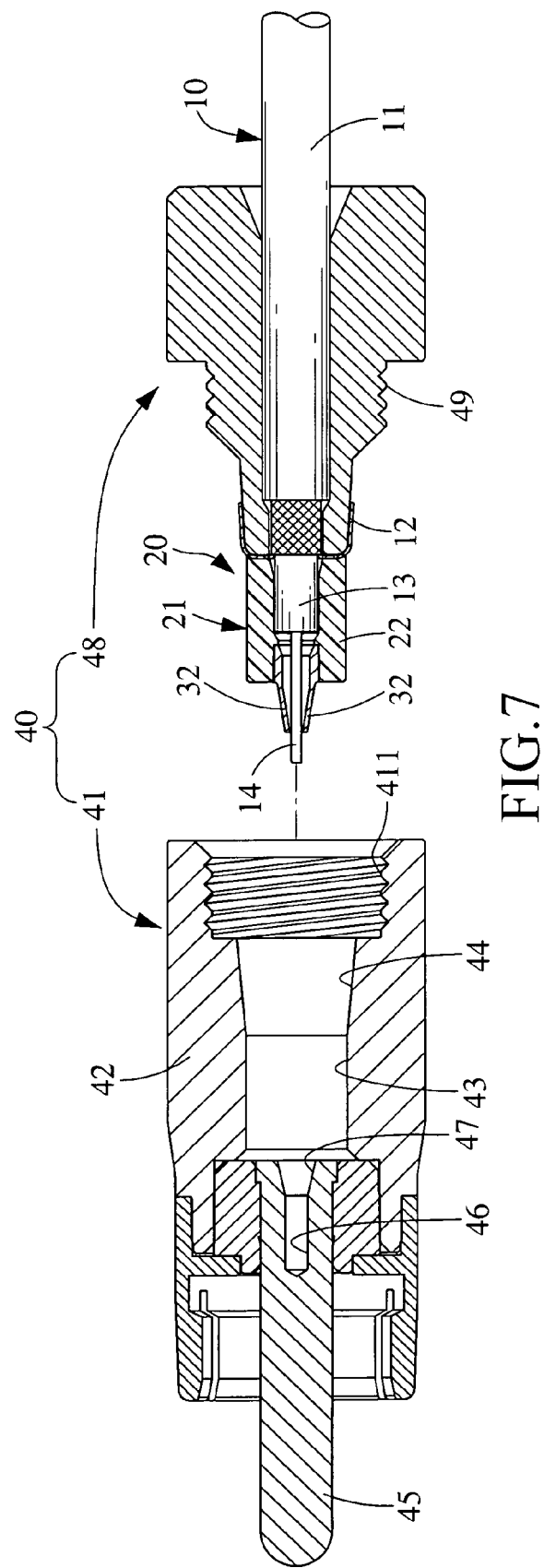
FIG.6
FIG.7

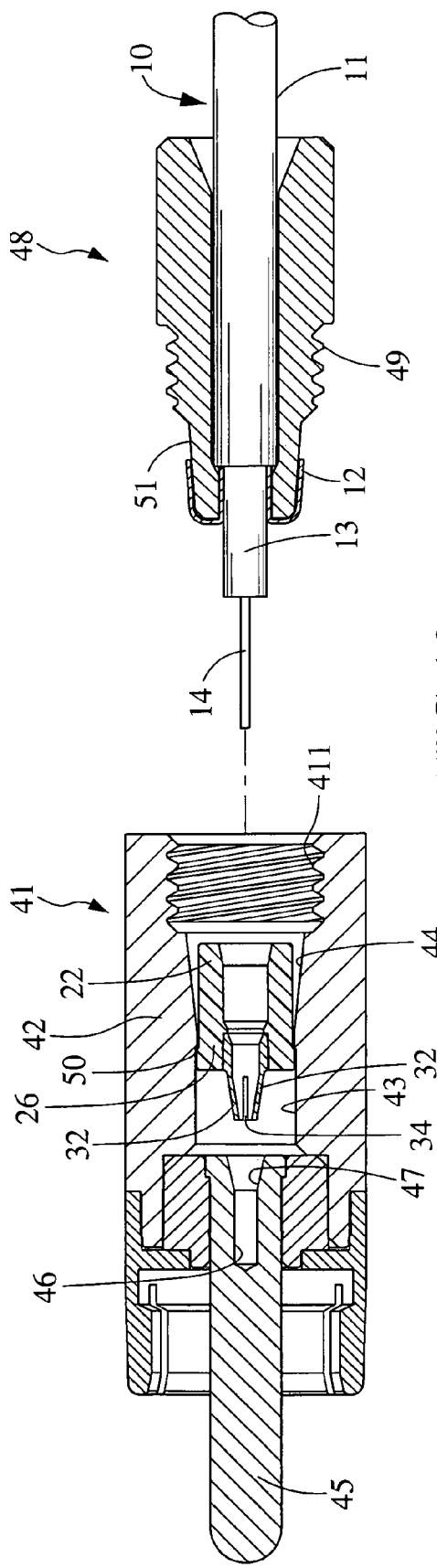
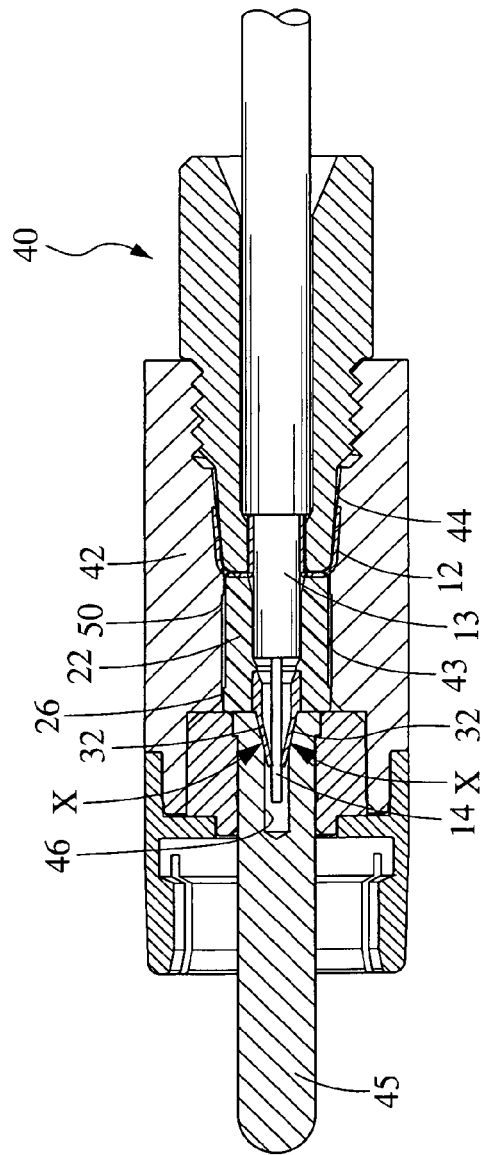
FIG.10
FIG.11

ADAPTER FOR MINI-COAXIAL CABLE

FIELD OF THE INVENTION

The present invention relates to an adapter for mini-coaxial cable, and more particularly to an adapter for easily connecting a mini-coaxial cable to a standard coaxial cable connector while ensuring good quality signal transmission.

BACKGROUND OF THE INVENTION

In signal transmission applications, the choice of coaxial cable for conducting the signal is usually determined by the distance between connection points, the signal frequency, the maximum bend radius required, and the connector space available in a particular transmitting and/or receiving device. The longer the cable and the higher the frequency used, the larger the outside diameter needs to be to prevent excessive signal loss. Traditional coaxial cable applications, such as cable TV, broadband data, and microwave signal transmission, employ coaxial cables with outer diameters of 0.25 to 1 inches for distance of 50 to 100 feet. In indoor equipment, the shorter distance requirements, typically 6-24 inches, the limitations of limited space and tighter bend radius requirements are overcome by using smaller coaxial cables with outer diameters of 0.1-0.14 inches. However, these small outer-diameter cables have to be used with a standard coaxial connector. FIG. 1 shows an existing technique for connecting mini-coaxial cables. The term "mini-coaxial cable" used throughout this document means a coaxial cable having a center conductor diameter larger than 0.1 mm and smaller than 0.8 mm, such as RG179 coaxial cable. As shown, a conventional mini-coaxial cable 10 includes an outer sheath 11, a braided sheath 12, an insulating spacer 13, and a center conductor 14; and a standard coaxial cable connector 15 includes an inner conducting body 16 and an insertion pin 17 for inserting into an axial guide way in the connector 15 to mechanically and electrically connect to the inner conducting body 16. The insertion pin 17 is provided in a rear end with a cylindrical recess 18. According to the prior art, the insertion pin 17 is first soldered to the center conductor 14 located at a stripped front end of the mini-coaxial cable 10. To solder the insertion pin 17 to the bare center conductor 14 requires electric power and clean and bright working environment. Once the mini-coaxial cable 10 with the insertion pin 17 soldered thereto has been assembled to the standard coaxial cable connector 15, the outer sheath 11 of the mini-coaxial cable 10 is clamped to the standard coaxial cable connector 15 using a known clamping tool.

The above-described manner of connecting the mini-coaxial cable to a standard coaxial cable connector is troublesome, and it is therefore desirable to develop a solder-free connecting structure for stably and firmly connecting the center conductor of a mini-coaxial cable to a standard coaxial cable connector.

SUMMARY OF THE INVENTION

A primary object of the present invention is to provide an easy and solder-free structure to give a bare center conductor of a mini-coaxial cable sufficient rigid support.

Another object of the present invention is to provide an adapter for mounting to a stripped front end of a mini-coaxial cable, in order to grip a bare center conductor of the mini-coaxial cable when the adapter is inserted into a standard coaxial cable connector.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein

FIG. 6 is an exploded sectioned side view showing the adapter of the present invention before being assembled to a center conductor of a mini-coaxial cable;

FIG. 7 is an exploded sectioned side view showing the adapter of the adapter of the present invention has been assembled to the center conductor of the mini-coaxial cable, and is about to be assembled to an inner conducting body of a standard coaxial cable connector;

FIG. 10 shows the adapter of FIG. 9 is slidably mounted in a main body of a standard coaxial cable connector for a center conductor of a mini-coaxial cable to insert thereinto; and FIG. 11 shows the adapter of FIG. 9 with the center conductor of the mini-coaxial cable inserted thereinto is displaced from a first position to a second position to electrically connect to the main body of the standard coaxial cable connector.

DETAILED DESCRIPTION OF THE PREFERRED EMBODIMENTS

Figure 2:
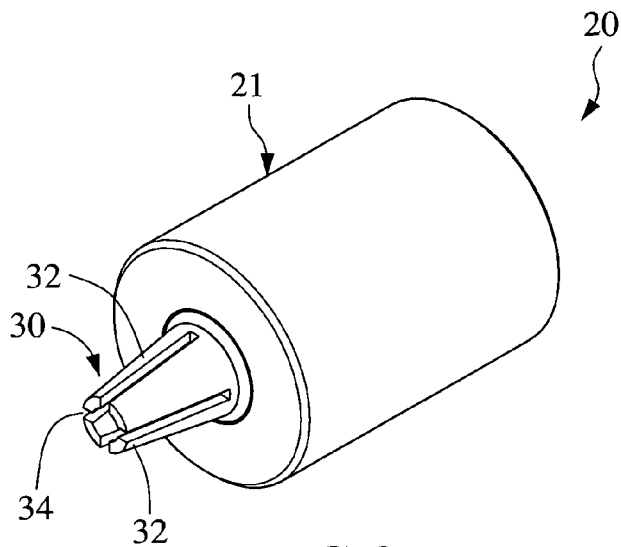
FIGS. 2 and 3 are perspective and sectioned side views, respectively, of an adapter for mini-coaxial cable according to a first preferred embodiment of the present invention.
Figure 3:
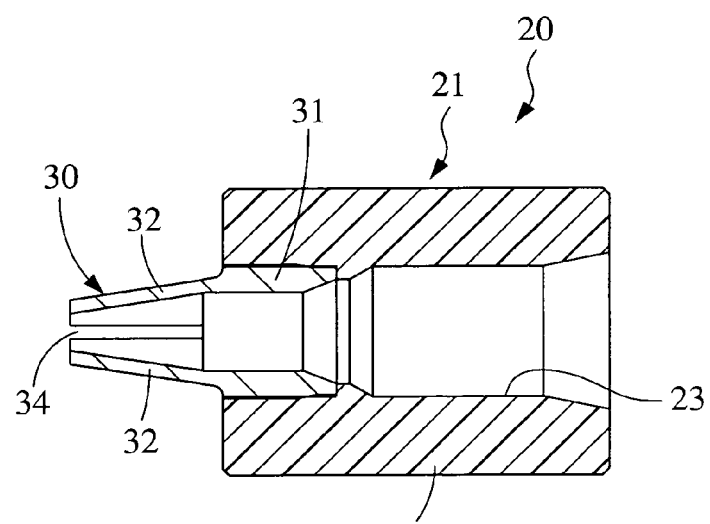

Please refer to FIGS. 2 and 3 that are perspective and sectioned side views, respectively, of an adapter for mini-coaxial cable according to a first preferred embodiment of the present invention. As shown, the adapter of the present invention is generally denoted a reference numeral 20, and includes a cylindrical member 21 and an electrically conductive insertion member 30.

Figure 1:
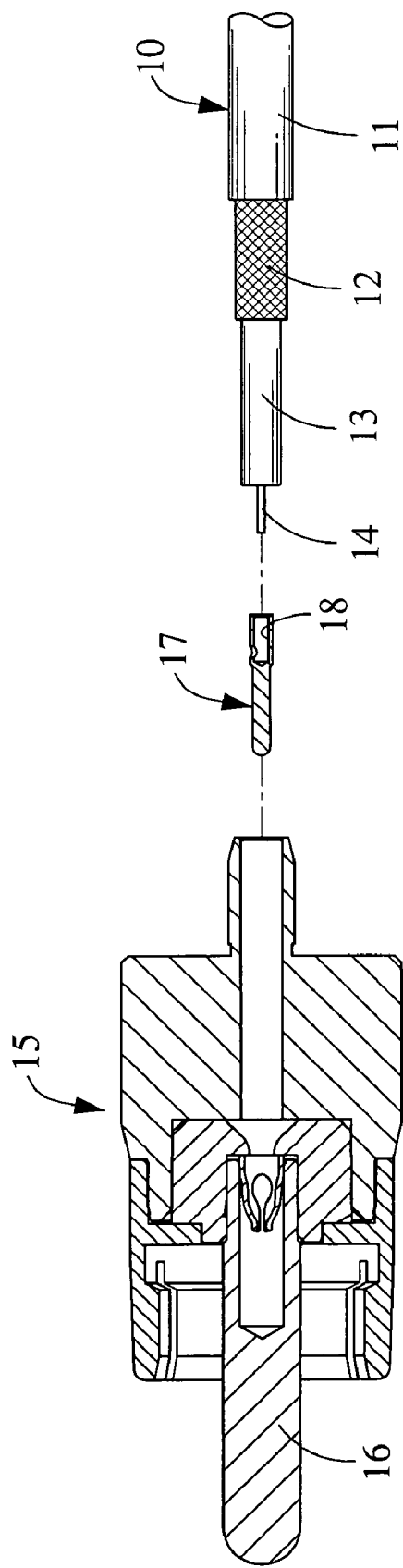
FIG. 1 is an exploded view showing a conventional coaxial cable connector.

As can be seen from both FIGS. 1 and 6, a conventional mini-coaxial cable 10 includes an outer sheath 11, a braided sheath 12, an insulating spacer 13, and a center conductor 14.

Figure 4:
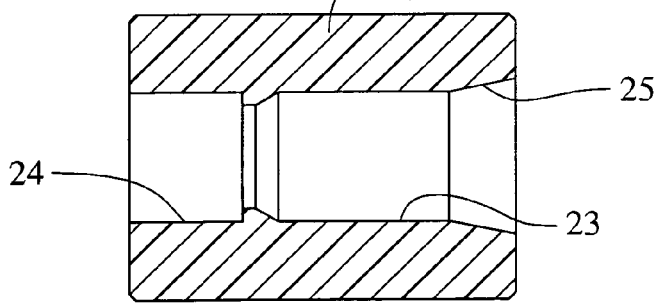
FIG. 4 is a sectioned side view of a cylindrical member for the adapter of the present invention.

FIG. 4 is a sectioned side view of the cylindrical member 21 of the adapter 20 according to the first embodiment the present invention. The cylindrical member 21 may be made of an electrically nonconductive material, and includes a tubular portion 22 internally defining a first receiving bore 23 and a second receiving bore 24 located before and communicable with the first receiving bore 23. The first receiving bore 23 has an inner diameter large enough for receiving the center conductor 14 and the insulating spacer 13 of the mini-coaxial cable 10 therein. The first receiving bore 23 has a rear portion formed into a forward tapered inner wall surface 25.

Figure 5:
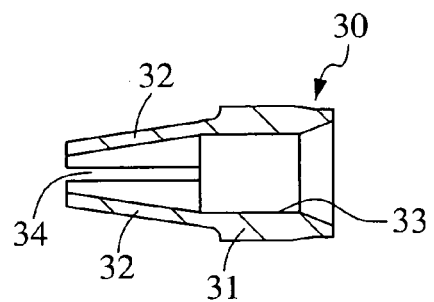
FIG. 5 is a sectioned side view of an insertion member for the adapter of the present invention.

FIG. 5 is a sectioned side view of the conducting insertion member 30 of the adapter 20 according to the first embodiment of the present invention. The insertion member 30 includes an annular portion 31 and a plurality of segments 32 forward extended from the annular portion 31. The annular portion 31 is tightly fitted in the second receiving bore 24 of the cylindrical member 21, and internally defines a hole 33. Any two adjacent segments 32 are spaced from each other by a slot 34 having a predetermined width.

Figure 8:
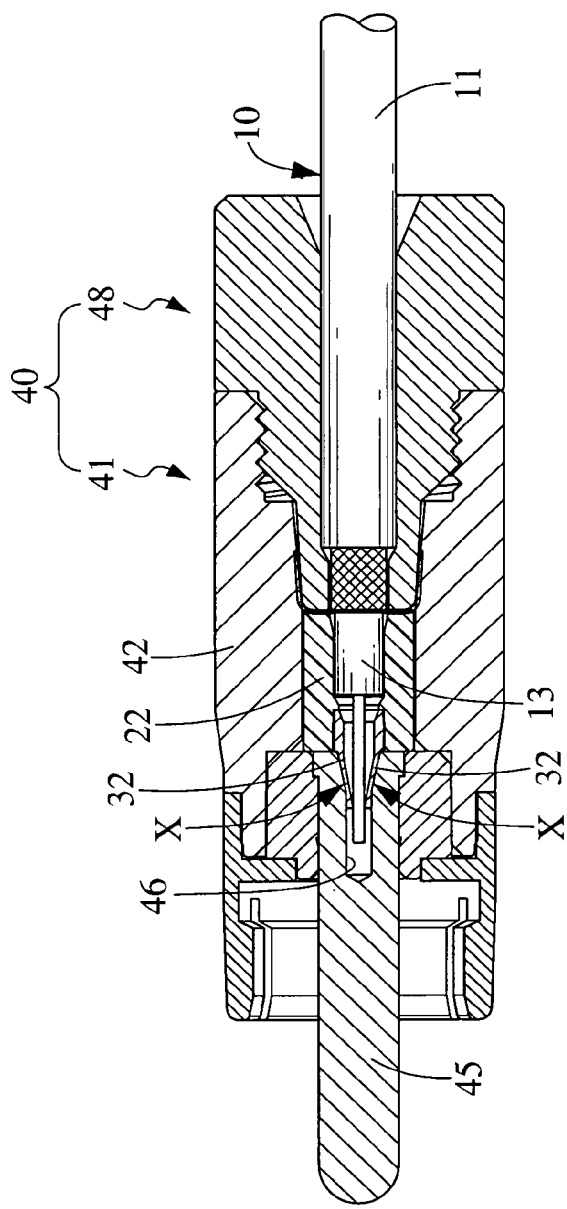
FIG. 8 is an assembled sectioned side view showing the adapter of the present invention has been fully inserted into an axial recess on the inner conducting body of the standard coaxial cable connector, so as to connect the mini-coaxial cable to the standard coaxial cable connector.

FIGS. 6 to 8 illustrate the manner of connecting the adapter 20 to a mini-coaxial cable 10 and a standard coaxial cable connector 40. The coaxial cable connector 40 may be differently configured connecting interfaces, such as F, BNC, RCA, and IEC connectors. The present invention will be described based on an RCA coaxial connector.

As shown, the coaxial cable connector 40 includes a main body 41 and a mating body 48. The main body 41 includes a cylindrical portion 42 internally defining an axially extended guide way 43, which has a rear part formed into a forward tapered bore 44. An inner conducting body 45 is provided in the main body 41, and has a cylindrical recess 46 formed in a rear portion thereof. A rear open end of the cylindrical recess 46 defines a forward tapered inner wall surface 47. The mating body 48 internally defines an axial space, in which the mini-coaxial cable 10 is received with a length of bare center conductor 14, insulating space 13, and braided sheath 12 projected from a front end of the mating body 48. Part of the projected braided sheath 12 is turned back to cover a forward tapered surface 51 of the front end of the mating body 48, as shown in FIG. 6.

The mini-coaxial cable 10 is then forward inserted into the adapter 20, so that the insulating spacer 13 is pushed into the first receiving bore 23 of the cylindrical member 21 and the bare center conductor 14 is extended through the segments 32 of the insertion member 30, as shown in FIG. 7.

Finally, the bare center conductor 14 with the adapter 20 assembled thereto is forward inserted into the axial guide way 43 in the main body 41 of the coaxial cable connector 40, and the mating body 48 is coupled with the main body 41 through a screwing mechanism or other known connecting manner. In the illustrated embodiment, the mating body 48 is provided at a predetermined position with external screw threads 49, and the main body 41 is provided in a rear end of the cylindrical portion 42 with internal screw threads 411, so that the mating body 48 is screwed to the main body 42 through engagement of the external screw threads 49 with the internal screw threads 411. When the segments 32 of the insertion member 30 are fully moved into the forward tapered inner wall surface 47 of the inner conducting body 45, the segments 32 are subjected to forces radially applied thereon by the tapered inner wall surface 47, as indicated by the arrows X in FIG. 8, and thereby firmly grip the bare center conductor 14. In this manner, the adapter 20 is firmly associated with the bare center conductor 14 and in good electrical contact with the inner conducting body 45. Meanwhile, with the mating body 48 fully screwed into the main body 41, the turned back braided sheath 12 is tightly compressed by the forward tapered bore 44 of the axial guide way 43 against the forward tapered surface 51 of the mating body 48 to ensure reliable electrical connection of the mini-coaxial cable 10 to the standard coaxial cable connector 40, and give the mini-coaxial cable 10 sufficient pull strength.

Figure 9:
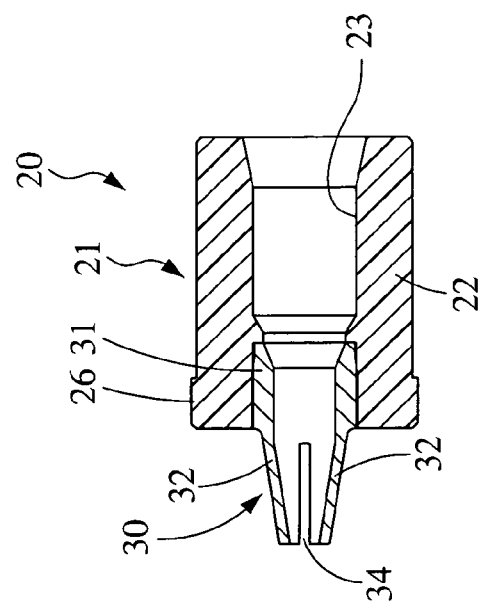
FIG. 9 is a sectioned side view of an adapter for mini-coaxial cable according to a second embodiment of the present invention.

FIG. 9 is a sectioned side view of an adapter 20 according to a second embodiment of the present invention, which is configured for pre-mounting in the main body 41 of the standard coaxial cable connector 40 to receive a bare center conductor 14 of the mini-coaxial cable 10. The adapter 20 in the second embodiment is generally structurally similar to the first embodiment shown in FIGS. 2 to 8, except for a radially outward flange 26 formed around a front end of the cylindrical member 21. To work with the adapter 20 according to the second embodiment of the present invention, the main body 41 of the standard coaxial cable connector 40 is provided between the guide way 43 and the forward tapered bore 44 with a shoulder portion 50. When the adapter 20 is pre-mounted in the main body 41, the flange 26 is received in the guide way 43 of the main body 41 and stopped by the shoulder portion 50 from rearward moving out of the guide way 43, as shown in FIG. 10. The adapter 20 slidably received in the guide way 43. When the bare center conductor 14 has been fully inserted into the adapter 20, the adapter 20 is pushed forward to axially slide from a first position toward a second position in the axial guide way 43 until the segments 32 of the insertion member 30 are fully moved into the forward tapered inner wall surface 47 of the inner conducting body 45. At this point, the segments 32 are subjected to forces radially applied thereon by the forward tapered inner wall surface 47, as indicated by the arrows X in FIG. 11, and thereby firmly grip the bare center conductor 14. In this manner, the adapter 20 is firmly associated with the bare center conductor 14 and in good electrical contact with the inner conducting body 45.

With the above arrangements, the present invention overcomes the drawbacks in the prior art. With the adapter 20 associated therewith, the bare center conductor 14 of the mini-coaxial cable 10, which is a very thin single wire or twisted wire, may have sufficient rigid support. The bare center conductor 14 may be easily inserted into the adapter 20 with a minor force, and then, the adapter 20 is pushed into the inner conducting body 45 of the main body 41 of the standard coaxial cable connector 40, so that the segments 32 of the adapter 20 are compressed by radially applied forces to tightly grip the bare center conductor 14.

The present invention has been described with some preferred embodiments thereof and it is understood that many changes and modifications in the described embodiments can be carried out without departing from the scope and the spirit of the invention that is intended to be limited only by the appended claims.

What is claimed is:

1. An adapter for mini-coaxial cable used to mechanically and electrically connect a mini-coaxial cable to a standard coaxial cable connector, the mini-coaxial cable including an outer sheath, a braided sheath, an insulating spacer, and a center conductor; a front end of the mini-coaxial cable being stripped by a predetermined length to bare the center conductor and expose the insulating spacer and the braided sheath thereat before connecting to the adapter and the standard coaxial cable connector; the adapter comprising:

a cylindrical member having a tubular portion internally defining a first receiving bore and a second receiving bore located before and communicable with the first receiving bore; the first receiving bore having an inner diameter large enough for receiving the bare center conductor and the exposed insulating spacer of the mini-coaxial cable therein; and an electrically conductive insertion member having a rear part and a front part coaxially extending therefrom, the rear part including tubular annular portion tightly fitted in the second receiving bore of the cylindrical member, and the front part including plurality of segments forward extended outside the second receiving bore for receiving the bare center conductor therebetween, the segments being biased apart one from the other;

whereby when the adapter is moved into the standard coaxial cable connector, the segments of the adapter are radially compressed by the standard coaxial cable connector to thereby tightly grip the bare center conductor received therein and ensure electrical connection of the mini-coaxial cable to the standard coaxial cable connector.

2. The adapter for mini-coaxial cable as claimed in claim 1, wherein any two adjacent ones of the segments are spaced from each other by a slot having a predetermined width.

3. The adapter for mini-coaxial cable as claimed in claim 1, wherein the standard coaxial cable connector includes a main body having an inner conducting body and an axially extended guide way provided therein; the inner conducting body being provided in a rear portion with a cylindrical recess and a forward tapered inner wall surface located behind the cylindrical recess; and wherein the segments on the insertion member of the adapter are radially compressed by the forward tapered inner wall surface of the inner conducting body to tightly grip the bare center conductor.

4. The adapter for mini-coaxial cable as claimed in claim 3, wherein the cylindrical member is formed around a front end thereof with a radially outward flange, which is slidably received in the axially extended guide way in the main body of the standard coaxial cable connector; and wherein the insulating spacer of the mini-coaxial cable received in the fist receiving bore may push the cylindrical member forward for the segments of the insertion member to move into the forward tapered inner wall surface of the inner conducting body.

5. The adapter for mini-coaxial cable as claimed in claim 4, wherein the flange on the cylindrical member is axially moved in the guide way from a first position to a second position, allowing the segments on the insertion member to move into the forward tapered inner wall surface of the inner conducting body and be radially compressed to tightly grip the bare center conductor.

6. The adapter for mini-coaxial cable as claimed in claim 3, wherein the standard coaxial cable connector further includes a mating body, and the mini-coaxial cable is received in the mating body with the exposed braided sheath turned back to cover a front end of the mating body; and the mating body is coupled with the main body through a screwing mechanism.

7. An adapter for mini-coaxial cable used to mechanically and electrically connect a mini-coaxial cable to a standard coaxial cable connector, the mini-coaxial cable including an outer sheath, a braided sheath, an insulating spacer, and a center conductor; a front end of the mini-coaxial cable being stripped by a predetermined length to bare the center conductor and expose the insulating spacer and the braided sheath thereat before connecting to the adapter and the standard coaxial cable connector; the adapter comprising:

a cylindrical member having a tubular portion internally defining a first receiving bore and a second receiving bore located before and communicable with the first receiving bore; the first receiving bore having an inner diameter large enough for receiving the bare center conductor and the exposed insulating spacer of the mini-coaxial cable therein; and an electrically conductive insertion member having an annular portion tightly fitted in the second receiving bore of the cylindrical member, and a plurality of segments forward extended from the annular portion for receiving the bare center conductor therebetween;

whereby when the adapter is moved into the standard coaxial cable connector, the segments of the adapter are radially compressed by the standard coaxial cable connector to thereby tightly grip the bare center conductor received therein and ensure electrical connection of the mini-coaxial cable to the standard coaxial cable connector;

wherein the standard coaxial cable connector includes a main body having an inner conducting body and an axially extended guide way provided therein; the inner conducting body being provided in a rear portion with a cylindrical recess and a forward tapered inner wall surface located behind the cylindrical recess; and wherein the segments on the insertion member of the adapter are radially compressed by the forward tapered inner wall surface of the inner conducting body to tightly grip the bare center conductor;

wherein the standard coaxial cable connector further includes a mating body, and the mini-coaxial cable is received in the mating body with the exposed braided sheath turned back to cover a front end of the mating body; and the mating body is coupled with the main body through a screwing mechanism; and, wherein the axially extended guide way has a rear part formed into a forward tapered bore, and the front end of the mating body is forward tapered corresponding to the forward tapered bore; and the turned back braided sheath is tightly compressed by the forward tapered bore of the guide way against the forward tapered front end of the mating body to achieve electrical connection of the mini-coaxial cable to the standard coaxial cable connector, and give the mini-coaxial cable sufficient pull strength.

* * * * *